United States Patent
Cray et al.

(10) Patent No.: US 9,635,827 B1
(45) Date of Patent: May 2, 2017

(54) ST. AUGUSTINE GRASS NAMED TBLL

(71) Applicant: NEW FRONTIER BRANDS PTY LTD, Advancetown (AU)

(72) Inventors: Robert Mark Cray, Advancetown (AU); Pamela Alexandra Cray, Advancetown (AU)

(73) Assignee: NEW FRONTIER BRANDS PTY LTD, Advancetown, Queensland (AU)

( * ) Notice: Subject to any disclaimer, the term of this patent is extended or adjusted under 35 U.S.C. 154(b) by 22 days.

(21) Appl. No.: 14/887,403

(22) Filed: Oct. 20, 2015

(51) Int. Cl.
| | |
|---|---|
| *A01H 5/10* | (2006.01) |
| *A01H 5/12* | (2006.01) |
| *A01H 1/02* | (2006.01) |
| *C12N 15/82* | (2006.01) |

(52) U.S. Cl.
CPC ............. *A01H 5/12* (2013.01); *A01H 1/02* (2013.01); *C12N 15/8241* (2013.01); *C12N 15/8274* (2013.01); *C12N 15/8275* (2013.01); *C12N 15/8277* (2013.01); *C12N 15/8278* (2013.01); *C12N 15/8279* (2013.01); *C12N 15/8286* (2013.01)

(58) Field of Classification Search
None
See application file for complete search history.

(56) References Cited

U.S. PATENT DOCUMENTS 5,523,520 A    6/1996  Hunsperger et al.
PP16,174 P3 *  12/2005 Layt .................. A01H 5/00

FOREIGN PATENT DOCUMENTS

AU    PBR 4613    9/2013

OTHER PUBLICATIONS

Eshed, et al., 1996, Less-than-additive epistatic interactions of quantitative trait loci in tomato, Genetics, 143:1807-1817.
Kraft, et al., 2000, Linkage disequilibrium and fingerprinting in sugar beet, Theor. Appl. Genet., 101:323-326.
New Frontier—reaching out to the future, TurfCraft: Turfgrass varieties, Dec. 11, 2014, Issue 159, pp. 26, 28.

* cited by examiner

*Primary Examiner* — Jason Deveau Rosen
(74) *Attorney, Agent, or Firm* — Jondle & Associates, P.C.

(57) ABSTRACT

A St. Augustine grass variety designated TBLL is disclosed. The invention relates to the seeds of St. Augustine grass variety TBLL, to the plants of St. Augustine grass variety TBLL, to the plant parts of St. Augustine grass variety TBLL, and to methods for producing progeny of St. Augustine grass variety TBLL. The invention also relates to methods for producing a St. Augustine grass plant containing in its genetic material one or more transgenes and to the transgenic St. Augustine grass plants and plant parts produced by those methods. The invention also relates to St. Augustine grass varieties or breeding cultivars, and plant parts derived from St. Augustine grass variety TBLL. The invention also relates to methods for producing other St. Augustine grass varieties, lines, or plant parts derived from St. Augustine grass variety TBLL, and to the St. Augustine grass plants, varieties, and their parts derived from use of those methods. The invention further relates to hybrid St. Augustine grass seeds, plants, and plant parts produced by crossing cultivar TBLL with another St. Augustine grass variety.

20 Claims, No Drawings

ST. AUGUSTINE GRASS NAMED TBLL

BACKGROUND OF THE INVENTION

The present invention relates to new variety of St. Augustine grass (*Stenotaphrum secundatum*) designated TBLL. All publications cited in this application are herein incorporated by reference.

Turfgrass plays a major role in our daily life. Turfgrass, from a beautification standpoint, provides a canvas for landscaped areas contributing to aesthetic appeal and adding to economic value. Recreational facilities include an array of sports fields, golf courses, parks and lawns. Turfgrass also provides functional value including dust control, erosion control, reduced surface temperatures and glare reduction.

Use and appearance are important considerations for turfgrass. To best serve a particular function, the turf should be suitable for the use for which it is intended and aesthetically appealing. Turfgrass should also be well-adapted to the environment where it will be planted. Based on climatic adaptation, turfgrass species have been placed into four categories: adapted for cool humid regions, warm humid regions, cool arid regions, and warm arid regions. The major turfgrasses adapted to the cool humid regions, and irrigated areas of the cool arid regions, are species of *Agrostis*, *Poa*, *Festuca*, and *Lolium*. In the warm humid and irrigated areas of the warm arid regions, the major adapted turfgrasses are species of *Cynodon*, *Zoysia*, *Stenotaphrum*, *Eremochloa*, *Paspalum*, *Festuca*, and *Agropyron*. In the non-irrigated warm arid regions, species of *Buchloe*, *Bouteloua* are *Cynodon* adapted.

St. Augustine grass (*Stenotaphrum secundatum*), also known as Buffalo grass, Charleston grass, and others, is a warm-season turfgrass that is adapted to warm, humid regions. St. Augustine grass is a fast-growing grass that has a medium to dark green color and coarse leaf texture. St. Augustine grass grows best in moist and somewhat fertile soils, but does normally not withstand waterlogged or droughty sites. St. Augustine grass has a high tolerance for heat, shade and soil salinity, but generally has poor tolerance for cold temperatures. Because St. Augustine grass is usually not wear tolerant, it is used for lawns and general purpose turf, but not for high traffic sports turf. With proper maintenance, St. Augustine grass will provide a dense, lush cover that effectively crowds out most weeds. The major insect pest of St. Augustine grass is the chinch bug and the major disease problem is St. Augustine grass decline virus (SADV).

A number of cultivars of St. Augustine grass have been developed, some of which are considered better for home lawns than others. Common St. Augustine grass has been grown since the 1800s and produces a light green, coarse, open lawn that is typically susceptible to chinch bugs and herbicide damage, cold, and shade damage. Bitterblue was selected from common St. Augustine grass in the 1930s for its finer leaf texture, darker blue-green color, and better turf density, but it is not resistant to chinch bugs or gray leaf spot disease. Other improved varieties include Floratam, Floratine, Floralawn, Raleigh and Seville.

Propagation of St. Augustine grass has historically been vegetative using stolons, plugs or sod in spite of the fact that some seed production has been noticed and attempted over the years. The problem has been that the commercial seed production has failed due to low levels of seed production and very low viability of the seed produced. Due to these difficulties, seed is not an established method to propagate St. Augustine grass.

It is therefore desirable to have St. Augustine grass with an improved, high-quality turf type that produces viable seed in sufficient quantity as to make seed production commercially viable.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

In one embodiment of the invention, there is provided a novel St. Augustine grass variety, botanically known as *Stenotaphrum secundatum*, and herein designated TBLL. This invention thus relates to the seeds of St. Augustine grass variety TBLL, to the plants or part(s) thereof of St. Augustine grass variety TBLL, to plants or part(s) thereof having all the phenotypic and morphological characteristics of St. Augustine grass variety TBLL, and to methods for producing a St. Augustine grass plant produced by crossing St. Augustine grass variety TBLL with itself or another St. Augustine grass variety, and the creation of variants by mutagenesis or transformation of St. Augustine grass variety TBLL.

In another aspect, the present invention provides regenerable cells for use in tissue culture of St. Augustine grass variety TBLL. The tissue culture will preferably be capable of regenerating plants having the physiological and morphological characteristics of St. Augustine grass variety TBLL. Preferably, the cells of such tissue culture will be embryos, meristematic cells, seeds, callus, pollen, leaves, anthers, pistils, roots, root tips, pods, flowers and stems. Protoplasts produced from such tissue culture are also included in the present invention. The St. Augustine grass plants regenerated from the tissue culture are also part of the invention.

Also included in the invention are methods for producing a St. Augustine grass plant produced by crossing St. Augustine grass variety TBLL with itself or another St. Augustine grass variety. When crossed with itself, i.e., when crossed with another St. Augustine grass variety TBLL plant or self-pollinated, St. Augustine grass variety TBLL will be conserved. When crossed with another, different St. Augustine grass plant, an $F_1$ hybrid seed is produced. $F_1$ hybrid seeds and plants produced by growing said hybrid seeds are included in the present invention. A method for producing an $F_1$ hybrid grass seed comprising crossing a St. Augustine grass variety TBLL plant with a different St. Augustine grass plant and harvesting the resultant hybrid St. Augustine grass seed are also part of the invention. The hybrid St. Augustine grass seed produced by the method comprising crossing a St. Augustine grass variety TBLL plant with a different St. Augustine grass plant and harvesting the resultant hybrid St. Augustine grass seed, are included in the invention, as are the hybrid St. Augustine grass plant or part(s) thereof, and seeds produced by growing said hybrid St. Augustine grass seed.

In another aspect, the present invention provides transformed St. Augustine grass variety TBLL plants or part(s) thereof that have been transformed so that its genetic material contains one or more transgenes, preferably operably linked to one or more regulatory elements. Also, the invention provides methods for producing a St. Augustine grass plant containing in its genetic material one or more transgenes, preferably operably linked to one or more regulatory elements, by crossing a transformed St. Augustine grass variety TBLL plant with either a second plant of another St. Augustine grass variety, or a non-transformed St. Augustine grass variety TBLL, so that the genetic material of the progeny that results from the cross contains the transgene(s), preferably operably linked to one or more regulatory elements. The invention also provides methods for producing a St. Augustine grass plant that contains in its genetic material one or more transgene(s), wherein the method comprises crossing the variety TBLL with a second St. Augustine grass variety of another St. Augustine grass variety which contains one or more transgene(s) operably linked to one or more regulatory element(s) so that the genetic material of the progeny that results from the cross contains the transgene(s) operably linked to one or more regulatory element(s). Transgenic St. Augustine grass cultivars, or part(s) thereof produced by the methods are in the scope of the present invention.

The invention further comprises methods for producing a male sterile St. Augustine grass plant, an herbicide resistant St. Augustine grass plant, an insect resistant St. Augustine grass plant, a disease resistant St. Augustine grass plant, a water stress tolerant St. Augustine grass plant, and a heat stress tolerant St. Augustine grass plant. Said methods comprise transforming a St. Augustine grass variety TBLL plant with a nucleic acid molecule that confers male sterility, herbicide resistance, insect resistance, disease resistance, water stress tolerance, or heat stress tolerance, respectively. The transformed St. Augustine grass plants, or part(s) thereof, obtained from the provided methods, including a male sterile St. Augustine grass plant, an herbicide resistant St. Augustine grass plant, an insect resistant St. Augustine grass plant, a disease resistant St. Augustine grass plant, a St. Augustine grass plant tolerant to water stress or a St. Augustine grass plant tolerant to heat stress are included in the present invention. For the present invention and the skilled artisan, disease is understood to be fungal diseases, viral diseases, bacterial diseases or other plant pathogenic diseases and a disease resistant plant will encompass a plant resistant to fungal, viral, bacterial and other plant pathogens.

In another aspect, the present invention provides for methods of introducing one or more desired trait(s) into St. Augustine grass variety TBLL and plants obtained from such methods. The desired trait(s) may be, but not exclusively, a single gene, preferably a dominant but also a recessive allele. Preferably, the transferred gene or genes will confer such traits as male sterility, herbicide resistance, insect resistance, resistance to bacterial, fungal, or viral disease, and tolerance to water stress or heat stress. The gene or genes may be naturally occurring gene(s) or transgene(s) introduced through genetic engineering techniques. The method for introducing the desired trait(s) is preferably a backcrossing process making use of a series of backcrosses to St. Augustine grass variety TBLL during which the desired trait(s) is maintained by selection.

In a preferred embodiment, the present invention provides methods for increasing and producing St. Augustine grass variety TBLL seed, whether by crossing a first parent St. Augustine grass variety plant with a second parent St. Augustine grass variety plant and harvesting the resultant St. Augustine grass seed, wherein both said first and second parent St. Augustine grass variety plant are the St. Augustine grass variety TBLL or by planting a St. Augustine grass seed of the St. Augustine grass variety TBLL, growing a St. Augustine grass variety TBLL plant from said seed, controlling a self pollination of the plant where the pollen produced by a grown St. Augustine grass variety TBLL plant pollinates the ovules produced by the very same St. Augustine grass variety TBLL grown plant, and harvesting the resultant seed. Additionally, St. Augustine grass variety TBLL may also be propagated vegetatively by stolons or other means.

The invention further provides methods for developing St. Augustine grass cultivars in a St. Augustine grass breeding program using plant breeding techniques including recurrent selection, backcrossing, pedigree breeding, molecular markers (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs). Amplified Fragment Length Polymorphisms (AFLPs), and Simple Sequence Repeats (SSRs) which are also referred to as Microsatellites, etc.) enhanced selection, genetic marker enhanced selection, and transformation. Seeds, St. Augustine grass plants, and part(s) thereof produced by such breeding methods are also part of the invention.

In addition to the exemplary aspects and embodiments described above, further aspects and embodiments will become apparent by study of the following descriptions.

DETAILED DESCRIPTION OF THE INVENTION

In the description and examples that follow, a number of terms are used. In order to provide a clear and consistent understanding of the specification and claims, including the scope to be given such terms, the following definitions are provided. If no definition is provided, all other technical and scientific terms used herein have the same meaning as is commonly understood by one of skill in the art to which the invention belongs.

Allele. An allele is any of one or more forms of a gene which relate to one trait or characteristic. In a diploid cell or organism, the two alleles of a given gene occupy corresponding loci on a pair of homologous chromosomes.

Alter. Alter refers to the utilization of up-regulation, down-regulation, or gene silencing.

Apomictic. As used herein, "apomictic" describes a plant that reproduces using apomixis.

Apomixis. Asexual reproduction in organisms that are also able to reproduce sexually, in which embryos are formed without fertilization or the creation of specialized reproductive cells.

Backcrossing. Backcrossing is a process in which a breeder repeatedly crosses hybrid progeny back to one of the parents, for example, a first generation hybrid $F_1$ with one of the parental genotypes of the $F_1$ hybrid.

Billbugs (*Sphenophorus parvulus*). A type of weevil or 'snout beetle' that damages cool season turfgrass by feeding below ground and damaging the roots or the growing crown area of the plant. Billbugs are some of the most difficult turfgrass insects to control because the adults' armor-like bodies do not readily absorb insecticides and the larvae bore inside grass stems for much of their lives.

Brown patch. A disease of St. Augustine grass caused by the fungus *Rhizoctonia solani* that usually causes thinned patches of light grown grass that are roughly circular in shape.

Cell. Cell as used herein includes a plant cell, whether isolated, in tissue culture or incorporated in a plant or plant part.

Chinch bug. Small insects that feed on stems of turfgrass. The hairy chichbug (*Blissus leucopterus*) is the most commonly encountered pest of northern turfgrasses. The southern chinch bug (*Blissus insularis*) is an insect pest of St. Augustine grass in the southern United States.

Commercial St. Augustine grass. A commercial St. Augustine grass is one which has been sold commercially.

Cotyledon. A cotyledon is a seed leaf.

Crossbreeding. As used herein, "crossbreeding" refers to the act of mating (crossing) individuals of different species or varieties of plants to produce hybrids.

Crown. The crown in grass is the area at which top growth and root growth originate.

Culm. The culm is the main aerial shoot to which leaves and inflorescences are attached. The culm is a rounded or slightly flattened stem with one or more solid joints known as nodes. The leaves are attached at the nodes and if the stem is not simple but branched, branches arise only at nodes. Roots may also develop from a node where the node comes into contact with the ground (as in decumbent and prostrate stems).

Embryo. The embryo is the small plant contained within a mature seed.

Endophyte. The term endophyte is applied to fungi which live symbiotically within plant tissues for all or part of their lifecycle and cause no apparent infections.

Gene. As used herein, "gene" refers to a segment of nucleic acid. A gene can be introduced into a genome of a species, whether from a different species or from the same species, using transformation or various breeding methods.

Gene silencing. The interruption or suppression of the expression of a gene at the level of transcription or translation.

Genotype. Refers to the genetic constitution of a cell or organism.

Grass flower or inflorescence. Flowers of grasses are borne in an inflorescence or flower head which terminates the culm and other branches of the stem. Smaller units of the inflorescence are called spikelets and these are arranged on one or more branches in a wide variety of different ways to which the standard terminology for inflorescences can be applied, but using the spikelet instead of the individual flower.

Gray leaf spot. A disease of St. Augustine grass caused by the fungus *Pyricularia grisea*, also referred to as *Magnaporthe grisea*, which causes oblong leaf spots.

Hybrid. Heterozygous offspring of two parents that differ in one or more inheritable characteristics.

Hypocotyl. A hypocotyl is the portion of an embryo or seedling between the cotyledons and the root. Therefore, it can be considered a transition zone between shoot and root.

Internode. The internodes act as spacers that distance one node from another.

Intercalary meristem. Intercalary meristem is a meristem at the base of the internode in monocot stems (particularly grass stems).

Linkage. Refers to a phenomenon wherein alleles on the same chromosome tend to segregate together more often than expected by chance if their transmission was independent.

Linkage disequilibrium. Refers to a phenomenon wherein alleles tend to remain together in linkage groups when segregating from parents to offspring, with a greater frequency than expected from their individual frequencies.

Node. A node in a grass stem is a solid point at which the intercalary meristem is located. The node also contains the bud that is capable of producing a new shoot. The terminal node contains the bud that produces the inflorescence.

Pedigree distance. Pedigree distance refers to the relationship among generations based on their ancestral links as evidenced in pedigrees. Pedigree distance may be measured by the distance of the pedigree from a given starting point in the ancestry.

Percent identity. Percent identity as used herein refers to the comparison of the homozygous alleles of two perennial St. Augustine grass varieties. Percent identity is determined by comparing a statistically significant number of the homozygous alleles of two developed varieties. For example, a percent identity of 90% between perennial St. Augustine grass variety 1 and perennial St. Augustine grass variety 2 means that the two varieties have the same allele at 90% of their loci.

Percent similarity. Percent similarity as used herein refers to the comparison of the homozygous alleles of one perennial St. Augustine grass variety with another St. Augustine grass plant, and if the homozygous allele of the first St. Augustine grass matches at least one of the alleles from the other plant then they are scored as similar. Percent similarity is determined by comparing a statistically significant number of loci and recording the number of loci with similar alleles as a percentage. A percent similarity of 90% between the first St. Augustine grass and another plant means that the first St. Augustine grass matches at least one of the alleles of the other plant at 90% of the loci.

Plant. As used herein, the term "plant" includes reference to an immature or mature whole plant, including a plant from which seed, roots or leaves have been removed. Seed or embryo that will produce the plant is also considered to be the plant.

Plant height. The length of the grass plant measured from the soil surface to the tip of the inflorescence.

Plant parts. As used herein, the term "plant parts" (or a perennial St. Augustine grass plant, or a part thereof) includes protoplasts, leaves, stems, roots, root tips, anthers, pistils, seed, embryo, pollen, ovules, cotyledon, hypocotyl, flower, shoot, tissue, petiole, cells, meristematic cells and the like.

Porpoising. 'Porpoising' is where stolon runners loop into aerial positions over an established or establishing sward without attachment to the soil.

Primary tillers. Primary tillers are shoots arising at the crown.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Resistance. As used herein, refers to the ability of a plant to withstand the deleterious effects of particular diseases, pests, or stresses, such as traffic or traffic simulation. "Increased resistance" refers to an increased ability of a plant to withstand deleterious effects of particular diseases, pests, or stresses, such as traffic or traffic simulation, when compared to a commercial variety.

Rhizome. A rhizome is a modified stem that grows underground Rhizomes are jointed (thus distinguishable from roots) with bladeless leaves (scales) arising from the joints Rhizomes enable a grass plant to spread horizontally as new culms develop vertically from the joints. Thus, grasses with extensive rhizome development will form a turf rather than distinct tufts or bunches.

Secondary tillers. Secondary tillers are tillers arising as branches of the primary tillers.

Single gene converted (Conversion). Single gene converted (conversion) plants refers to plants which are developed by a plant breeding technique called backcrossing wherein essentially all of the desired morphological and physiological characteristics of a variety are recovered in addition to the single gene transferred into the variety via the backcrossing technique or via genetic engineering.

Single sequence repeats (SSR). Also referred to as microsatellites, SSR markers are short sequences of nucleotides that are repeated in tandem. SSRs are very polymorphic due to high mutation rates affecting the number of repeat units and the polymorphisms can easily be detected on high resolution gels by running PCR amplified fragments obtained using a unique pair of primers flanking the repeat. SSRs allow the identification of many alleles at a single locus.

St. Augustine grass (Stenotaphrum secundatum). A coarse-textured, warm-season turfgrass that is adapted to warm, humid regions. Also known as Charleston grass and Buffalo grass or Buffalo turf, and sometimes as carpetgrass.

St. Augustine grass decline virus (SADV or SAD). A viral disease of St. Augustine grass that causes grass blades to develop a mottled, chlorotic appearance that can eventually spread across large sections of turf. Caused by Panicum mosaic virus.

Stem rust. Caused by the fungus Puccinia graminis, is a serious disease of turfgrass that attacks the parts of the plant that are above ground.

Stolon. A stolon is a stem that creeps across the surface of the ground, and is really a basal branch of the culm that will develop roots and shoots from some or all of its nodes. Like a rhizome, a stolon results in a spreading or turf forming grass plant.

Sward. Surface layer of ground containing a mat of grass and grass roots.

Tensile strength. Means the amount of force in pounds required to tear a piece of sod in two. Tensile strength is determined with a mechanical sod stretcher coupled to a device to measure force in pounds. Tensile strength, tear point and sod strength are used interchangeably.

Tiller. A tiller is another name for a grass stem.

Tiller length. Tiller length is measured in centimeters from the lowest node to the last node subtending the green foliage.

Tolerance. The ability of a variety such as TBLL to tolerate a biotic or abiotic stress/condition.

Traffic. As used herein, "traffic" or "wear" refers to any kind of movement over turfgrass, or pressure applied to turfgrass, especially by foot, athletic play, vehicles, or artificially applied by a traffic simulator, resulting in damage to the turfgrass.

Traffic tolerance. Also referred to as "wear tolerance". Refers to the ability of turfgrass to withstand damage from traffic.

Transgene. A gene that is transferred from an organism of one species to an organism of another species by genetic engineering.

Turf density. As used herein, refers to the percentage of soil surface covered by the canopy of the turf.

Turfgrass. Any of the various grasses, such as St. Augustine grass or perennial ryegrass, grown to form turf Turf is a surface layer of earth containing a dense growth of grass and its matted roots; also called sod.

Variety. A taxonomic subdivision of a species consisting of naturally occurring or selectively bred populations or individuals that differ from the remainder of the species in certain minor characteristics. Used interchangeably with the term cultivar to denote a group of individuals that are distinct genetically from other groups of individuals in the same species.

Vernalization. Vernalization induces plants to begin the reproductive cycle after exposure to cold temperatures and short day length. The amount of cold exposure and short day lengths required varies with the species.

Wear. Also referred to as "traffic"; see "traffic".

White grubs. Destructive insect pests of turfgrasses. Turfgrass is damaged throughout the summer when the grubs (the larval or immature stages of certain beetles) chew off the grass roots just below the soil surface and the resulting root injury reduces the turf's ability to take up water and nutrients and withstand the stress of hot, dry weather conditions. Many species of white grubs can cause this damage, including but not limited to the larvae of masked chafers, Japanese beetles, green June beetles, May beetles and black turfgrass Ataenius beetle. Control of various white grubs has become increasingly difficult since the loss of persistent chlorinated hydrocarbon insecticides.

The following detailed description is of the currently contemplated modes of carrying out the invention. The description is not to be taken in a limiting sense, but is made merely for the purpose of illustrating the general principles of the invention, since the scope of the invention is best defined by the appended claims.

The present invention relates to a new and distinct St. Augustine grass plant designated TBLL and botanically known as Stenotaphrum secundatum. An individual plant was initially discovered in September 2002 by the inventors growing on hard shale among "common" bermudagrass (Cynodon dactylon) and "common" Swazi grass (Digitaria didactyla) in Advancetown, Queensland, Australia. The selection was made on the basis that the genotype was deep green in colour, had prostrate growth, was well adapted to the shaded environment and the few inflorescence (spike-like panicles) were visible. This individual plant was taken to the breeder's home for breeding research, multiplication, selection between segregates and testing of segregates. More specifically, the plant was asexually propagated to produce a number of segregating plants that were planted in the ground next to vegetative St. Augustine plant material of Palmetto (SS-100), Shademaster, Sir Walter and ST-91. The breeders placed all grasses under significant stress for a period of 6 years; the significant stresses included mowing pressure (mowing regularly at reduced heights), drought stress, shade simulation and with the application of pesticides and growth regulators, including high repetitive rates of trinexapac-ethyl.

Following testing, a single improved and new vegetative plant was selected because it displayed a deeper green colour, maintained better health during drought, maintained better turf quality when grown in shade and produced a tighter sward under close routine mowing compared with the initial individual progenitor plant and the other St. Augustine grasses trialled. The selection was designated as 'TBLL' of the present invention. TBLL was asexually propagated for over 3 generations between 2008 and 2010. After further observation and testing of TBLL by the breeder between 2012 and 2014 it was identified that TBLL produced deeper more vigorous roots, comprised of shorter internodes and leaf blades and produced significant amounts of inflorescence when left unmown in comparison to the original plant collected in Advancetown. TBLL also unexpectedly reproduced by both sexual (apomixis) and asexual (vegetative) means. To date, 3 generations of TBLL have been produced apomictically which have remained distinct, uniform and stable as TBLL.

St. Augustine grass variety TBLL of the present invention is an improved turf type that is already considered unique due to its improved vegetative turf characteristics and growth habits, but the ability of TBLL to produce viable seed of the quality and quantity to make commercial seed production viable distinguishes this variety as truly novel for this species. St. Augustine grass variety TBLL has a high inflorescence density and seed production, as well as superior root development, with visible roots down to 1 meter plus depth. Additionally, TBLL has prostrate lateral growth with little to no 'porpoising' with medium internode spacings present. Overall, St. Augustine grass variety TBLL is a high quality, high density, deep rooting cultivar with a deep green colour that produces viable seed for commercial sales.

St. Augustine grass variety TBLL has the following morphologic and other characteristics (based primarily on data collected in Queensland, Australia). Colour references are to the Royal Horticultural Society (RHS) Colour Chart, 5$^{th}$ edition, 2007.

Table 1

Variety Description Information

Classification:
Family: Poaceae
Botanical: *Stenotaphrum secundatum*
Common name: St. Augustine grass
Variety name: TBLL
Plant:
Habit: Creeping
Type: Mat-forming
Height: Medium
Diameter (of spaced plants after 133 days post planting): 79.10 cm
Longevity: Perennial
Spreading: Via stolons
Propagation method: Seed or vegetative
Stolon:
Nodes: Compound with two leaves
Number of branches at node two from stolon tip: 0.80
Number of branches at node three from stolon tip: 2.18
Number of branches at node four from stolon tip: 2.17
Number of branches at node five from stolon tip: 2.08
Number of branches at node six from stolon tip: 2.00
Internode length: Medium
Internode thickness: Medium
Length of fourth internode from stolon tip: 30.84 mm
Diameter of fourth internode from stolon tip: 3.01 mm
Length of leaf sheath on fourth visible node from stolon tip: 13.61 mm
Length of leaf blade on fourth visible node from stolon tip: 13.04 mm
Width of leaf blade on fourth visible node from stolon tip: 4.48 mm
Colour when exposed to sunlight: RHS N77A
Leaf Blade:
Texture of surface: Glabrous
Apex: Acute
Length: Medium
Width: Medium
Colour: RHS 137B
Length of unmown culms: Medium
Ligule hairs: Fringe of hairs
Inflorescence:
Position: Terminal or axillary
Type: Solid panicle
Central axis: Flattened
Texture: Corky
Toughness: Tough
Density (number per m$^2$): 50.13
Length of racemes: Medium to long
Appearance of racemes: Unilateral
Spikelets:
Type: Deciduous
Number of sessile spikelets per raceme: 1 to 4
Length: 69.34 mm
Width: 3.99 mm
Breadth: 2.03 mm
Peduncle length: Medium to long
Peduncle thickness: Medium to fine
Flowering tillers:
Length of sheath on flag leaf: 36.74 mm
Length of blade on flag leaf: 17.47 mm
Width of blade on flag leaf: 5.25 mm
Length of sheath on fourth leaf: 19.12 mm
Length of blade on fourth leaf: 29.64 mm
Width of blade on fourth leaf: 6.25 mm
Length of fourth internode: 15.48 mm
Diameter of fourth internode: 1.69 mm
Length of peduncle: 41.04 mm
Diameter of peduncle: 1.40 mm
Number of spikes present on inflorescence bearing tillers: 2.38
Sward:
Unmown sward height 203 days post planting: 13.13 cm It should be understood, of course, that the foregoing relates to exemplary embodiments of the invention and that modifications may be made without departing from the spirit and scope of the invention as set forth in the following claims.

FURTHER EMBODIMENTS OF THE INVENTION

Choice of breeding or selection methods depends on the mode of plant reproduction, the heritability of the trait(s) being improved, and the type of cultivar used commercially (e.g., F$_1$ hybrid cultivar, pureline cultivar, etc.). Popular selection methods commonly include population formation by hybridization, genomic selection, marker assisted selection, recurrent selection, mutation breeding, single-seed descent, bulk selection, pedigree selection, modified pedigree selection, and mass selection.

Breeding Methods

The following describes breeding methods that may be used with St. Augustine grass variety TBLL in the development of further St. Augustine grass plants. One such embodiment is a method for developing a cultivar TBLL progeny St. Augustine grass plant in a St. Augustine grass plant breeding program comprising: obtaining the St. Augustine grass plant, or a part thereof, of cultivar TBLL utilizing said plant or plant part as a source of breeding material and selecting a St. Augustine grass cultivar TBLL progeny plant with molecular markers in common with variety TBLL and/or with morphological and/or physiological characteristics described herein.

Another method involves producing a population of St. Augustine grass variety TBLL progeny St. Augustine grass plants, comprising crossing cultivar TBLL with another St. Augustine grass plant, thereby producing a population of St. Augustine grass plants, which, on average, derive 50% of their alleles from St. Augustine grass variety TBLL. A plant of this population may be selected and repeatedly selfed or sibbed with a St. Augustine grass cultivar resulting from these successive filial generations. In some embodiments, the St. Augustine grass cultivar produced by this method and that has obtained at least 50% of its alleles from St. Augustine grass variety TBLL.

One of ordinary skill in the art of plant breeding would know how to evaluate the traits of two plant varieties to determine if there is no significant difference between the two traits expressed by those varieties. For example, see Fehr and Walt, *Principles of Cultivar Development*, p 261-286 (1987). Thus the methods and variety described herein includes St. Augustine grass cultivar TBLL progeny St. Augustine grass plants comprising a combination of at least two cultivar TBLL traits or the cultivar TBLL combination of traits listed in the Summary of the Invention, so that said progeny St. Augustine grass plant is not significantly different for said traits than St. Augustine grass variety TBLL as determined at the 5% significance level when grown in the same environmental conditions. Using techniques described herein, molecular markers may be used to identify said progeny plant as a St. Augustine grass variety TBLL progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of St. Augustine grass variety TBLL may also be characterized through their filial relationship with St. Augustine grass variety TBLL, as for example, being within a certain number of breeding crosses of St. Augustine grass variety TBLL. A breeding cross is a cross made to introduce new genetics into the progeny, and is distinguished from a cross, such as a self or a sib cross, made to select among existing genetic alleles. The lower the number of breeding crosses in the pedigree, the closer the relationship between St. Augustine grass variety TBLL and its progeny. For example, progeny produced by the methods described herein may be within 1, 2, 3, 4 or 5 breeding crosses of St. Augustine grass variety TBLL.

Recurrent selection is a method used in a plant breeding program to improve a population of plants. TBLL is suitable for use in a recurrent selection program. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties. The number of parental plant varieties, populations, wild accessions, ecotypes, etc., that are used to generate a synthetic can vary from as little as 10 to as much as 500. Typically, about 100 to 300 varieties, populations, etc., are used a parents for the synthetic variety. Seed from the parental seed production plot of a synthetic variety can be sold to the farmer. Alternatively, seed from the parental seed production plot can subsequently undergo one or two generations of multiplication, depending on the amount of seed produced in the parental plot and the demand for seed.

Mass selection is a useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Mutation breeding is another method of introducing new traits into St. Augustine grass variety TBLL. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (such as from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, 1993. *Principles of Cultivar Development*, Macmillan Publishing Company. In addition, mutations created in other St. Augustine grass plants may be used to produce a backcross conversion of St. Augustine grass variety TBLL that comprises such mutation.

Breeding with Molecular Markers

Molecular markers, which include markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing St. Augustine grass variety TBLL.

Isozyme Electrophoresis and RFLPs have been widely used to determine genetic composition. Shoemaker and Olsen, (O'Brien, S. J., (ed.) 1993. *Genetic Maps: Locus Maps of Complex Genomes*. Cold Spring Harbor Laboratory Press. Cold Spring Harbor, New York.), developed a molecular genetic linkage map that consisted of 25 linkage groups with about 365 RFLP, 11 RAPD (random amplified polymorphic DNA), three classical markers, and four isozyme loci. See also, Shoemaker R. C. 1994. "RFLP Map of Soybean" p 299-309 In R. L. Phillips and I. K. Vasil (ed.) *DNA-Based Markers in Plants*. Kluwer Academic Press Dordrecht, the Netherlands. In switchgrass, Missaoui also described RFLP markers (Missaoui et al., 2006, "Molecular markers for the classification of switchgrass (*Panicum virgatum* L.) germplasm and to assess genetic diversity in three synthetic switchgrass populations" *Genetic Resources and Crop Evolution* 53:1291-1302).

SSR technology is currently the most efficient and practical marker technology; more marker loci can be routinely used and more alleles per marker locus can be found using SSRs in comparison to RFLPs. For example Diwan and Cregan, described a highly polymorphic microsatellite loci in soybean with as many as 26 alleles. (Diwan, N., and P. B. Cregan. 1997 "Automated sizing of fluorescent-labeled simple sequence repeat (SSR) markers to assay genetic variation in soybean". *Theor. Appl. Genet.* 95:220-225). Single Nucleotide Polymorphisms (SNPs) may also be used to identify the unique genetic composition of TBLL and progeny varieties retaining that unique genetic composition. Various molecular marker techniques may be used in combination to enhance overall resolution.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Gene Conversions

When the term "St. Augustine grass plant" is used in the context of the methods and varieties described herein, this also includes any gene conversions of that variety. The term gene converted plant as used herein refers to those St. Augustine grass plants which are developed by a plant breeding technique called backcrossing wherein essentially all of the desired morphological and physiological characteristics of a variety are recovered in addition to the one or more genes transferred into the variety via the backcrossing technique. Backcrossing methods can be used with the methods and variety described herein to improve or introduce one or more characteristics into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental St. Augustine grass plant that contributes the gene(s) for the desired characteristic is termed the nonrecurrent or donor parent. This terminology refers to the fact that the nonrecurrent parent is used one time in the backcross protocol and therefore does not recur. The parental St. Augustine grass plant to which the gene or genes from the nonrecurrent parent are transferred is known as the recurrent parent as it is used for several rounds in the backcrossing protocol (Poehlman & Sleper, 1994; Fehr, *Principles of Cultivar Development* pp. 261-286 (1987)). In a typical backcross protocol, the original variety of interest (recurrent parent) is crossed to a second variety (nonrecurrent parent) that carries the gene(s) of interest to be transferred. The resulting progeny from this cross are then crossed again to the recurrent parent and the process is repeated until a St. Augustine grass plant is obtained wherein essentially all of the desired morphological and physiological characteristics of the recurrent parent are recovered in the converted plant, in addition to the transferred gene(s) from the nonrecurrent parent.

The selection of a suitable recurrent parent is an important step for a successful backcrossing procedure. The goal of a backcross protocol is to alter or substitute one or more traits or characteristics in the original variety. To accomplish this, one or more genes of the recurrent variety is/are modified or substituted with the desired gene(s) from the nonrecurrent parent, while retaining essentially all of the rest of the desired genetic, and therefore the desired physiological and morphological, constitution of the original variety. The choice of the particular nonrecurrent parent will depend on the purpose of the backcross; one of the major purposes is to add some agronomically important trait to the plant. The exact backcrossing protocol will depend on the characteristic(s) or trait(s) being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic(s) has been successfully transferred.

Many traits have been identified that are not regularly selected for in the development of a new variety but that can be improved by backcrossing techniques. Traits may or may not be transgenic; examples of these traits include but are not limited to, male sterility, herbicide resistance, resistance for bacterial, fungal, or viral disease, insect resistance, male fertility, enhanced nutritional quality, industrial usage, yield stability and yield enhancement. These genes are generally inherited through the nucleus. Several of these traits are described in U.S. Pat. Nos. 5,959,185; 5,973,234 and 5,977,445; the disclosures of which are specifically hereby incorporated by reference for this purpose.

Introduction of a New Trait or Locus into TBLL

Variety TBLL represents a new base genetic variety into which a new locus or trait may be introgressed. Direct transformation and backcrossing represent two important methods that can be used to accomplish such an introgression. The term backcross conversion and locus conversion are used interchangeably to designate the product of a backcrossing program.

Backcross Conversions of TBLL

A backcross conversion of TBLL occurs when DNA sequences are introduced through backcrossing (Poehlman, *Breeding Field Crops*, p. 204 (1987), with TBLL utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., "Marker-assisted Selection in Backcross Breeding" In: *Proceedings Symposium of the Analysis of Molecular Data*, August 1994, Crop Science Society of America, Corvallis, Oreg., where it is demonstrated that a backcross conversion can be made in as few as two backcrosses.

The complexity of the backcross conversion method depends on the type of trait being transferred (single genes or closely linked genes vs unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See Hallauer et al. in *Corn and Corn Improvement*, Sprague and Dudley, Third Ed. 1998). Desired traits that may be transferred through backcross conversion include, but are not limited to, sterility (nuclear and cytoplasmic), fertility restoration, nutritional enhancements, drought tolerance, nitrogen utilization, altered fatty acid profile, altered carbohydrate profile, industrial enhancements, disease resistance (bacterial, fungal or viral), insect resistance and herbicide resistance. In addition, an introgression site itself, such as an FRT site, Lox site or other site-specific integration site, may be inserted by backcrossing and utilized for direct insertion of one or more genes of interest into a specific plant variety. In some embodiments, the number of loci that may be backcrossed into TBLL is at least 1, 2, 3, 4, or 5 and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of a site-specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, *Breeding Field Crops*, p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant and easily recognized traits.

One process for adding or modifying a trait or locus in St. Augustine grass variety TBLL comprises crossing TBLL plants grown from TBLL seed with plants of another St. Augustine grass variety that comprise the desired trait or locus, selecting $F_1$ progeny plants that comprise the desired trait or locus to produce selected $F_1$ progeny plants, crossing the selected progeny plants with the TBLL plants to produce backcross progeny plants, selecting for backcross progeny plants that have the desired trait or locus and the morphological characteristics of St. Augustine grass variety TBLL to produce selected backcross progeny plants; and backcrossing to TBLL three or more times in succession to produce selected fourth or higher backcross progeny plants that comprise said trait or locus. The modified TBLL may be further characterized as having the physiological and morphological characteristics of St. Augustine grass variety TBLL and/or may be characterized by percent similarity or identity to TBLL as determined by SSR markers. The above method may be utilized with fewer backcrosses in appropriate situations, such as when the donor parent is highly related or markers are used in the selection step. Desired traits that may be used include those nucleic acids known in the art, some of which are mentioned herein, that will affect traits through nucleic acid expression or inhibition. Desired loci include the introgression of FRT, Lox and other sites for site specific integration, which may also affect a desired trait if a functional nucleic acid is inserted at the integration site.

Pedigree Breeding

Pedigree breeding starts with the crossing of two genotypes, such as TBLL and another St. Augustine grass variety having one or more desirable characteristics that is lacking or which complements TBLL. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding, successive filial generations will serve to increase seed of the developed variety. In some embodiments, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a St. Augustine grass variety may be crossed with another variety to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the non-recurrent parent. This approach leverages the value and strengths of the recurrent parent for use in new St. Augustine grass varieties.

Therefore, an embodiment is a method of making a backcross conversion of St. Augustine grass variety TBLL, comprising the steps of crossing a plant of St. Augustine grass variety TBLL with a donor plant comprising a desired trait, selecting an $F_1$ progeny plant comprising the desired trait, and backcrossing the selected $F_1$ progeny plant to a plant of St. Augustine grass variety TBLL. This method may further comprise the step of obtaining a molecular marker profile of St. Augustine grass variety TBLL and using the molecular marker profile to select for a progeny plant with the desired trait and the molecular marker profile of TBLL. In one embodiment the desired trait is a mutant gene or transgene present in the donor parent.

In addition, the above process and other similar processes described herein may be used to produce first generation progeny St. Augustine grass seed by adding a step at the end of the process that comprises crossing TBLL with the introgressed trait or locus with a different St. Augustine grass plant and harvesting the resultant first generation progeny St. Augustine grass seed.

Transgenic St. Augustine Grass

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are inserted into the genome using transformation, are referred to herein collectively as "transgenes". In some embodiments of the invention, transgenic variants of the St. Augustine grass variety of the present invention may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years several methods for producing transgenic plants have been developed, and the present invention also relates to transgenic variants of the claimed St. Augustine grass variety of the present invention.

One embodiment of the invention is a process for producing St. Augustine grass varieties further comprising a desired trait, said process comprising transforming a St. Augustine grass plant with a transgene that confers a desired trait. Another embodiment is the product produced by this process. In one embodiment the desired trait may be one or more of herbicide resistance, insect resistance, or disease resistance. The specific gene may be any known in the art or listed herein, including: a polynucleotide conferring resistance to imidazolinone, sulfonylurea, glyphosate, glufosinate, triazine, benzonitrile, cyclohexanedione, phenoxy proprionic acid and L-phosphinothricin; a polynucleotide encoding a *Bacillus thuringiensis* polypeptide, or a polynucleotide conferring resistance to one or more nematodes, *Phytophthora* root rot, or other fungi, or one or more viruses.

Numerous methods for plant transformation have been developed, including biological and physical plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67-88 and Armstrong, "The First Decade of Maize Transformation: A Review and Future Perspective" (Maydica 44:101-109, 1999). In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119. See also, for example, Qu, et. al., Turfgrass, Chapter 8, in Compendium of Transgenic Crop Plants: Transgenic Plantation Crops, Ornamentals and Turf Grasses, edited by C. Kole and T. C. Hall, 2008, 42 pages.

A genetic trait which has been engineered into the genome of a particular St. Augustine grass plant may then be moved into the genome of another St. Augustine grass variety using traditional breeding techniques that are well known in the plant breeding arts. For example, a backcrossing approach is commonly used to move a transgene from a transformed St. Augustine grass variety into an already developed St. Augustine grass variety, and the resulting backcross conversion plant would then comprise the transgene(s).

Various genetic elements can be introduced into the plant genome using transformation. These elements include, but are not limited to genes, coding sequences, inducible, constitutive, and tissue specific promoters, enhancing sequences, and signal and targeting sequences. For example, see the traits, genes and transformation methods listed in U.S. Pat. No. 6,118,055.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed St. Augustine grass plants using transformation methods as described below to incorporate transgenes into the genetic material of the St. Augustine grass plant(s).

Expression Vectors for St. Augustine Grass Transformation: Marker Genes

Expression vectors include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., Proc. Natl. Acad. Sci. USA, 80:4803 (1983). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford et al., Plant Physiol. 86:1216 (1988), Jones et al., Mol. Gen. Genet., 210:86 (1987), Svab et al., Plant Mol. Biol. 14:197 (1990), Hille et al., Plant Mol. Biol. 7:171 (1986)). Other selectable marker genes confer resistance to herbicides such as glyphosate, glufosinate or bromoxynil (Comai et al., Nature 317:741-744 (1985), Gordon-Kamm et al., Plant Cell 2:603-618 (1990) and Stalker et al., Science 242:419-423 (1988)).

Selectable marker genes for plant transformation not of bacterial origin include, for example, mouse dihydrofolate reductase, plant 5-enolpyruvylshikimate-3-phosphate synthase and plant acetolactate synthase (Eichholtz et al., Somatic Cell Mol. Genet. 13:67 (1987), Shah et al., Science 233:478 (1986), Charest et al., Plant Cell Rep. 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase (Jefferson, R. A., Plant Mol. Biol. Rep. 5:387 (1987), Teeri et al., EMBO J. 8:343 (1989), Koncz et al., Proc. Natl. Acad. Sci. USA 84:131 (1987), DeBlock et al., EMBO J. 3:1681 (1984)).

In vivo methods for visualizing GUS activity that do not require destruction of plant tissue are available (Molecular Probes publication 2908, IMAGENE GREEN, p. 1-4 (1993) and Naleway et al., J. Cell Biol. 115:151a (1991)). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells (Chalfie et al., Science 263:802 (1994)). GFP and mutants of GFP may be used as screenable markers.

Expression Vectors for St. Augustine Grass Transformation: Promoters

Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, flowers, anthers, fibers, xylem vessels, tracheids, or sclerenchyma. Such promoters are referred to as "tissue-preferred". Promoters that initiate transcription only in a certain tissue are referred to as "tissue-specific". A "cell-type" specific promoter primarily drives expression in certain cell types in one or more organs, for example, vascular cells in roots or leaves. An "inducible" promoter is a promoter which is induced or activated in the presence of the correct stimulus. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters—An inducible promoter is operably linked to a gene for expression. Optionally, the inducible promoter is operably linked to a nucleotide sequence encoding a signal sequence which is operably linked to a gene for expression in perennial St. Augustine grass. With an inducible promoter the rate of transcription increases in response to an inducing agent.

Any inducible promoter can be used in the instant invention. See Ward et al., Plant Mol. Biol. 22:361-366 (1993). Exemplary inducible promoters include, but are not limited to, that from the ACEI system which responds to copper (Mett et al., Proc. Natl. Acad. Sci. USA 90:4567-4571 (1993)); In2 gene from maize which responds to benzenesulfonamide herbicide safeners (Hershey et al., Mol. Gen Genetics 227:229-237 (1991) and Gatz et al., Mol. Gen. Genetics 243:32-38 (1994)) or Tet repressor from Tn10 (Gatz et al., Mol. Gen. Genetics 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., Proc. Natl. Acad. Sci. USA 88:0421 (1991)).

B. Constitutive Promoters—A constitutive promoter is operably linked to a gene for expression in perennial St. Augustine grass or the constitutive promoter is operably linked to a nucleotide sequence encoding a signal sequence which is operably linked to a gene for expression in St. Augustine grass.

Many different constitutive promoters can be utilized in the instant invention. Exemplary constitutive promoters include, but are not limited to, the promoters from plant viruses such as the 35S promoter from CaMV (Odell et al., Nature 313:810-812 (1985)) and the promoters from such genes as rice actin (McElroy et al., Plant Cell 2: 163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)). The ALS promoter, Xbal/Ncol fragment 5' to the *Brassica napus* ALS3 structural gene (or a nucleotide sequence similarity to said Xbal/Ncol fragment), represents a particularly useful constitutive promoter. See PCT application WO 96/30530.

C. Tissue-specific or Tissue-preferred Promoters—A tissue-specific promoter is operably linked to a gene for expression in St. Augustine grass. Optionally, the tissue-specific promoter is operably linked to a nucleotide sequence encoding a signal sequence which is operably linked to a gene for expression in St. Augustine grass. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai et al., Science 23:476-482 (1983) and Sengupta-Gopalan et al., Proc. Natl. Acad. Sci. USA 82:3320-3324 (1985)); a leaf-specific and light-induced promoter such as that from cab or rubisco (Simpson et al., EMBO J. 4(11): 2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zml3 (Guerrero et al., Mol. Gen. Genetics 244:161-168 (1993)) or a microspore-preferred promoter such as that from apg (Twell et al., Sex. Plant Reprod. 6:217-224 (1993)).

Signal Sequences for Targeting Proteins to Subcellular Compartments

Transport of a protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., Plant Mol. Biol. 20:49 (1992); Knox, C., et al., Plant Mol. Biol. 9:3-17 (1987); Lerner et al., Plant Physiol. 91:124-129 (1989); Frontes et al., Plant Cell 3:483-496 (1991); Matsuoka et al., Proc. Natl. Acad. Sci. 88:834 (1991); Gould et al., J. Cell. Biol. 108:1657 (1989); Creissen et al., Plant J. 2:129 (1991); Kalderon, et al., Cell 39:499-509 (1984); Steifel, et al., Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

Wang et al. discuss "Large Scale Identification, Mapping and Genotyping of Single-Nucleotide Polymorphisms in the Human Genome", Science, 280:1077-1082, 1998, and similar capabilities are becoming available for the St. Augustine grass genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques. SNPs may also be used alone or in combination with other techniques.

Likewise, by means of the present invention, plants can be genetically engineered to express various phenotypes of interest. Through the transformation of St. Augustine grass the expression of genes can be altered to enhance disease resistance, insect resistance, herbicide resistance and other traits. DNA sequences native to St. Augustine grass as well as non-native DNA sequences can be transformed into St. Augustine grass and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, The Maize Handbook ch. 118 (Springer-Verlag 1994) or other genetic elements such as a FRT, Lox or other site specific integration site, antisense technology (see, e.g., Sheehy et al. (1988) PNAS USA 85:8805-8809; and U.S. Pat. Nos. 5,107,065; 5,453,566; and 5,759,829); co-suppression (e.g., Taylor (1997) Plant Cell 9:1245; Jorgensen (1990) Trends Biotech. 8(12):340-344; Flavell (1994) PNAS USA 91:3490-3496; Finnegan et al. (1994) Bio/Technology 12: 883-888; and Neuhuber et al. (1994) Mol. Gen. Genet. 244:230-241); RNA interference (Napoli et al. (1990) Plant Cell 2:279-289; U.S. Pat. No. 5,034,323; Sharp (1999) Genes Dev. 13:139-141; Zamore et al. (2000) Cell 101:25-33; and Montgomery et al. (1998) PNAS USA 95:15502-15507), virus-induced gene silencing (Burton, et al. (2000) Plant Cell 12:691-705; and Baulcombe (1999) Curr. Op. Plant Bio. 2:109-113); target-RNA-specific ribozymes (Haseloff et al. (1988) Nature 334: 585-591); hairpin structures (Smith et al. (2000) Nature 407:319-320; WO 99/53050; and WO 98/53083); MicroRNA (Aukerman & Sakai (2003) Plant Cell 15:2730-2741); ribozymes (Steinecke et al. (1992) EMBO J. 11:1525; and Perriman et al. (1993) Antisense Res. Dev. 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Likewise, by means of the present invention, additional genes of interest can be expressed in transformed plants. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example Jones et al., Science 266:789 (1994) (cloning of the tomato Cf-9 gene for resistance to Cladosporium fulvum); Martin et al., Science 262:1432 (1993) (tomato Pto gene for resistance to Pseudomonas syringae pv. tomato encodes a protein kinase); Mindrinos et al. Cell 78:1089 (1994) (Arabidopsis RSP2 gene for resistance to Pseudomonas syringae), McDowell & Woffenden, (2003) Trends Biotechnol. 21(4): 178-83 and Toyoda et al., (2002) Transgenic Res. 11 (6): 567-82.

B. A gene conferring resistance to a pest, such as a nematode. See e.g., PCT Application WO 96/30517; PCT Application WO 93/19181.

C. A Bacillus thuringiensis protein, a derivative thereof or a synthetic polypeptide modeled thereon. See, for example, Geiser et al., Gene 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US 93/06487 which teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*); Chattopadhyay et al. (2004) *Critical Reviews in Microbiology* 30 (1): 33-54 2004; Zjawiony (2004) *J Nat Prod* 67 (2): 300-310; Carlini & Grossi-de-Sa (2002) *Toxicon,* 40 (11): 1515-1539; Ussuf et al. (2001) *Curr Sci.* 80 (7): 847-853; and Vasconcelos & Oliveira (2004) *Toxicon* 44 (4): 385-403. See also U.S. Pat. No. 5,266,317 to Tomalski et al., which discloses genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene, U.S. Pat. Nos. 7,145,060, 7,087,810 and 6,563,020.

L. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M. A hydrophobic moment peptide. See PCT application WO 95/16776 and U.S. Pat. No. 5,580,852, which disclose peptide derivatives of tachyplesin which inhibit fungal plant pathogens, and PCT application WO 95/18855 and U.S. Pat. No. 5,607,914 which teaches synthetic antimicrobial peptides that confer disease resistance.

N. A membrane permease, a channel former or a channel blocker. For example, see the disclosure of Jaynes et al., *Plant Sci* 89:43 (1993), of heterologous expression of a cecropin-β lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus and tobacco mosaic virus.

P. An insect-specific antibody or an immunotoxin derived therefrom. Thus, an antibody targeted to a critical metabolic function in the insect gut would inactivate an affected enzyme, killing the insect. See Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

S. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S., *Current Biology,* 5(2) (1995); Pieterse & Van Loon (2004) *Curr. Opin. Plant Bio.* 7(4):456-64 and Somssich (2003) *Cell* 113(7):815-6.

U. Antifungal genes. See Cornelissen and Melchers, *Plant Physiol.*, 101:709-712 (1993); Parijs et al., *Planta* 183:258-264 (1991) and Bushnell et al., *Can. J. of Plant Path.* 20(2):137-149 (1998). Also see U.S. Pat. No. 6,875,907.

V. Detoxification genes, such as for fumonisin, beauvericin, moniliformin and zearalenone and their structurally related derivatives. For example, see U.S. Pat. No. 5,792,931.

W. Cystatin and cysteine proteinase inhibitors. See U.S. Pat. No. 7,205,453.

X. Defensin genes. See WO 03/000863 and U.S. Pat. No. 6,911,577.

Y. Genes that confer resistance to *Phytophthora* root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif. (1995).

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids, aryloxyphenoxy propionate, and cyclohexanediones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,566,587; 6,338,961; 6,248,876 B1; U.S. Pat. Nos. 6,040,497; 5,804,425; 5,633,435; 5,145,783; 4,971,908; 5,312,910; 5,188,642; 4,940,835; 5,866,775; 6,225,114 B1; U.S. Pat. Nos. 6,130,366; 5,310,667; 4,535,060; 4,769,061; 5,633,448; 5,510,471; Re. 36,449; RE 37,287 E; and 5,491,288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. application Ser. No. 10/427,692. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall et al., *Theon. Appl. Genet.* 83:435 (1992).

C. An herbicide that inhibits photosynthesis, such as a triazine (psbA and gs+ genes) and a benzonitrile (nitrilase gene). Przibila et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441 and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., *Plant Physiol.*, 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

5. Genes that Create a Site for Site Specific DNA Integration.

This includes the introduction of FRT sites that may be used in the FLP/FRT system and/or Lox sites that may be used in the Cre/Loxp system. For example, see Lyznik, et al., Site-Specific Recombination for Genetic Engineering in Plants, *Plant Cell Rep* (2003) 21:925-932 and WO 99/25821, which are hereby incorporated by reference. Other systems that may be used include the Gin recombinase of phage Mu (Maeser et al., 1991; Vicki Chandler, The Maize Handbook ch. 118 (Springer-Verlag 1994), the Pin recombinase of *E. coli* (Enomoto et al., 1983), and the R/RS system of the pSR1 plasmid (Araki et al., 1992).

6. Genes that Affect Abiotic Stress Resistance.

Genes that affect abiotic stress resistance (including but not limited to flowering, pod and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. No. 5,892,009, U.S. Pat. No. 5,965,705, U.S. Pat. No. 5,929,305, U.S. Pat. No. 5,891,859, U.S. Pat. No. 6,417,428, U.S. Pat. No. 6,664,446, U.S. Pat. No. 6,706,866, U.S. Pat. No. 6,717,034, U.S. Pat. No. 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; US 2004/0148654 and WO 01/36596 where abscisic acid is altered in plants resulting in improved plant phenotype such as increased yield and/or increased tolerance to abiotic stress; WO 2000/006341, WO 04/090143, U.S. application Ser. No. 10/817,483 and U.S. Pat. No. 6,992,237 where cytokinin expression is modified resulting in plants with increased stress tolerance, such as drought tolerance, and/or increased yield. Also see WO 02/02776, WO 2003/052063, JP2002281975, U.S. Pat. No. 6,084,153, WO 01/64898, U.S. Pat. Nos. 6,177,275 and 6,107,547 (enhancement of nitrogen utilization and altered nitrogen responsiveness). For ethylene alteration, see US 20040128719, US 20030166197 and WO 2000/32761. For plant transcription factors or transcriptional regulators of abiotic stress, see e.g. US 20040098764 or US 20040078852.

Other genes and transcription factors that affect plant growth and agronomic traits such as yield, flowering, plant growth and/or plant structure, can be introduced or introgressed into plants, see e.g. WO 97/49811 (LHY), WO 98/56918 (ESD4), WO 97/10339 and U.S. Pat. No. 6,573,430 (TFL), U.S. Pat. No. 6,713,663 (FT), WO 96/14414 (CON), WO 96/38560, WO 01/21822 (VRN1), WO 00/44918 (VRN2), WO 99/49064 (GI), WO 00/46358 (FRI), WO 97/29123, U.S. Pat. No. 6,794,560, U.S. Pat. No. 6,307,126 (GAI), WO 99/09174 (D8 and Rht), and WO 2004/076638 and WO 2004/031349 (transcription factors).

Methods for St. Augustine Grass Transformation

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc. Boca Raton, 1993) pages 67-88. In addition, expression vectors and in-vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). See also, for example, Longo, et al., *Agrobacterium* Protocols: Turf Grasses, in Methods in Molecular Biology, 344: 83-95(2007). Descriptions of *Agrobacterium* vector systems and methods for *Agrobacterium*-mediated gene transfer are provided by Gruber et al., supra, Miki et al., supra and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987); Sanford, J. C., *Trends Biotech.* 6:299 (1988); Klein et al., *Bio/Tech.* 6:559-563 (1988); Sanford, J. C. *Physiol Plant* 7:206 (1990); Klein et al., *Biotechnology* 10:268 (1992). See also U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.*, 4:2731 (1985); Christou et al., *Proc Natl. Acad. Sci. USA* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described (Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994)).

Following transformation of St. Augustine grass target tissues, expression of the above-described selectable marker genes allows for preferential selection of transformed cells, tissues and/or plants, using regeneration and selection methods well known in the art.

Genetic Marker Profile Through SSR and First Generation Progeny

In addition to phenotypic observations, a plant can also be identified by its genotype. The genotype of a plant can be characterized through a genetic marker profile which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Cregan et. al, "An Integrated Genetic Linkage Map of the Soybean Genome" *Crop Science* 39:1464-1490 (1999), and Berry et al., Assessing Probability of Ancestry Using Simple Sequence Repeat Profiles: Applications to Maize Inbred Lines and Soybean Varieties" *Genetics* 165:331-342 (2003).

Particular markers used for these purposes are not limited to any particular set of markers, but are envisioned to include any type of marker and marker profile which provides a means of distinguishing varieties.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

Tissue Culture

Further reproduction of the St. Augustine grass varieties of the present invention can occur by tissue culture and regeneration. Tissue culture of various tissues of St. Augustine grass and regeneration of plants therefrom is well known and widely published. For example, reference may be had to Bradley, D. E. et al. 2001. Effects of cultivar, explant treatment, and medium supplements on callus induction and plantlet regeneration in perennial ryegrass. *Int. Turfgrass Soc. Res. J.* 9:152-156; Cao, M. X., et al. 2006. Transformation of recalcitrant turfgrass cultivars through improvement of tissue culture and selection regime. *Plant, Cell, Tissue Organ Culture.* 85:307-316; WenZhen, L. et al. Factors effecting on tissue culture of perennial ryegrass (*Lolium perenne* L.). *Forest Res.* 2004. 17:95-101. See also, for example, Qu, et. al., Turfgrass, Chapter 8, in Compendium of Transgenic Crop Plants: Transgenic Plantation Crops, Ornamentals and Turf Grasses, edited by C. Kole and T. C. Hall, 2008, 42 pages. Thus, another aspect of this invention is to provide cells which upon growth and differentiation produce St. Augustine grass plants having the physiological and morphological characteristics of the St. Augustine grass plants of the present invention.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, culms, leaves, stems, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Tables

The following tables are provided to further illustrate the present invention and are not intended to limit the invention beyond the limitations set forth in the appended claims. The following tables characterize the outstanding traits and characteristics of St. Augustine grass variety TBLL compared to the closest St. Augustine grass varieties and standards.

Table 2 shows morphological characteristics of St. Augustine grass variety TBLL compared to the closest known commercial varieties from trials grown in Queensland, Australia in 2012. The comparison varieties included St. Augustine grasses B12, Sir Walter, SS100, and TF01. Thirty spaced plants of each variety were arranged in six randomized blocks with five plants per plot. Table 2, column 1 shows the characteristic, column 2 shows the results for St. Augustine grass variety TBLL, column 3 shows the results for B12, column 4 shows the results for Sir Walter, column 5 shows the results for SS100, and column 6 shows the results for TF01. An asterisk (*) indicates data not available.

TABLE 2

| Characteristic | TBLL | B12 | Sir Walter | SS100 | TF01 |
| --- | --- | --- | --- | --- | --- |
| Plant: habit | creeping | creeping | creeping | creeping | creeping |
| Plant: type | mat-forming | mat-forming | mat-forming | mat-forming | mat-forming |
| Plant: height | medium | medium to tall | medium to tall | medium | medium to tall |
| Plant: longevity | perennial | perennial | perennial | perennial | perennial |
| Plant: spreading | stolons | stolons | stolons | stolons | stolons |
| Stolon: nodes | compound nodes with 2 leaves | compound nodes with 2 leaves | compound nodes with 2 leaves | compound nodes with 2 leaves | compound nodes with 2 leaves |
| Stolon: internode length | medium | medium | long | medium | long |
| Stolon: internode thickness | medium | medium to broad | medium to broad | medium to broad | medium to broad |
| Stolon: colour when exposed to sunlight | N77A | N200A | N186C | N199A | N77A |
| Unmown culms: length | medium | medium to long | medium to long | medium to long | medium to long |
| Leaf blade: texture of surface | glabrous | glabrous | glabrous | glabrous | glabrous |
| Leaf blade: apex | acute | acute | broad-acute | acute | acute |
| Leaf blade: length | medium | medium | medium to long | medium | medium |
| Leaf blade: width | medium | medium | medium to broad | medium to broad | medium |
| Leaf blade: colour | 137B | 137C | 137B | 137B | 137C |
| Ligule: hairs | fringe of hairs | fringe of hairs | fringe of hairs | fringe of hairs | fringe of hairs |
| Inflorescence: position | terminal or axillary | * | terminal or axillary | * | terminal or axillary |
| Inflorescence: type | solid panicle | * | laterally compressed solid panicle | * | compressed solid panicle |
| Inflorescence: central axis | flattened | * | flattened | * | flattened |
| Inflorescence: texture | corky | * | corky | * | corky |
| Inflorescence: toughness | tough | * | tough | * | tough |

TABLE 2-continued

| Characteristic | TBLL | B12 | Sir Walter | SS100 | TF01 |
|---|---|---|---|---|---|
| Inflorescence: length of racemes | medium to long | * | medium to long | * | medium |
| Inflorescence: number of sessile spikelets per raceme | 1-4 | * | 1-4 | * | 1-3 |
| Inflorescence: appearance of racemes | unilateral | * | unilateral | * | unilateral |
| Spikelets: type | deciduous | * | deciduous | * | deciduous |
| Peduncle: length | medium to long | * | medium to long | * | medium |
| Peduncle: thickness | medium to fine | * | medium to long | * | medium to fine |

Table 3 shows quantitative and statistically analyzed characteristics of St. Augustine grass variety TBLL compared to the closest known commercial varieties from trials grown in Queensland, Australia in 2012. *The comparison varieties included St.* Augustine grasses B12, Sir Walter, SS100, and TF01. Thirty spaced plants of each variety were arranged in six randomized blocks with five plants per plot. Table 3, column 1 shows the characteristic, column 2 shows the results for St. Augustine grass variety TBLL, column 3 shows the results for B12, column 4 shows the results for Sir Walter, column 5 shows the results for SS100, and column 6 shows the results for TF01. $P<0.01$ indicates that probability is less than or equal to one percent. An asterisk (*) indicates data not available and 'ns' indicates not statistically significant.

TABLE 3

| Characteristic | TBLL | B12 | Sir Walter | SS100 | TF01 |
|---|---|---|---|---|---|
| Plant: mean plant diameter of spaced plants after 133 days post planting (cm) | | | | | |
| Mean | 79.10 | 65.60 | 115.80 | 69.30 | 123.10 |
| Std. Deviation | 14.20 | 16.80 | 20.50 | 10.60 | 25.00 |
| LSD/sig | 19.1 | ns | P ≤ 0.01 | ns | P ≤ 0.01 |
| Stolon node: number of branches at node two from stolon tip | | | | | |
| Mean | 0.80 | 1.65 | 1.13 | 1.35 | 1.20 |
| Std. Deviation | 0.95 | 0.90 | 0.91 | 0.63 | 0.68 |
| LSD/sig | 0.42 | P ≤ 0.01 | ns | P ≤ 0.01 | ns |
| Stolon node: number of branches at node three from stolon tip | | | | | |
| Mean | 2.18 | 2.60 | 2.12 | 2.12 | 2.30 |
| Std. Deviation | 0.47 | 0.49 | 0.42 | 0.32 | 0.50 |
| LSD/sig | 0.25 | P ≤ 0.01 | ns | ns | ns |
| Stolon node: number of branches at node four from stolon tip | | | | | |
| Mean | 2.17 | 2.68 | 2.22 | 2.12 | 2.55 |
| Std. Deviation | 0.38 | 0.50 | 0.45 | 0.32 | 0.50 |
| LSD/sig | 0.24 | P ≤ 0.01 | ns | ns | P ≤ 0.01 |
| Stolon node: number of branches at node five from stolon tip | | | | | |
| Mean | 2.08 | 2.23 | 2.03 | 2.10 | 2.40 |
| Std. Deviation | 0.33 | 0.43 | 0.32 | 0.30 | 0.49 |
| LSD/sig | 0.20 | ns | ns | ns | P ≤ 0.01 |
| Stolon node: number of branches at node six from stolon tip | | | | | |
| Mean | 2.00 | 2.25 | 2.08 | 2.15 | 2.28 |
| Std. Deviation | 0.00 | 0.44 | 0.28 | 0.36 | 0.45 |
| LSD/sig | 0.19 | P ≤ 0.01 | ns | ns | P ≤ 0.01 |
| Stolon: length of fourth internode from stolon tip (mm) | | | | | |
| Mean | 30.84 | 29.72 | 40.23 | 34.64 | 41.35 |
| Std. Deviation | 4.84 | 6.37 | 6.89 | 4.85 | 6.92 |
| LSD/sig | 3.27 | ns | P ≤ 0.01 | P ≤ 0.01 | P ≤ 0.01 |

TABLE 3-continued

| Characteristic | TBLL | B12 | Sir Walter | SS100 | TF01 |
|---|---|---|---|---|---|
| Stolon: diameter of fourth internode from stolon tip (mm) | | | | | |
| Mean | 3.01 | 2.55 | 3.13 | 3.15 | 3.25 |
| Std. Deviation | 0.45 | 0.46 | 0.41 | 0.34 | 0.53 |
| LSD/sig | 0.25 | P ≤ 0.01 | ns | ns | ns |
| Stolon: length of leaf sheath on fourth visible node from stolon tip (mm) | | | | | |
| Mean | 13.61 | 12.55 | 17.01 | 17.52 | 15.37 |
| Std. Deviation | 2.50 | 3.29 | 3.24 | 2.53 | 2.52 |
| LSD/sig | 1.57 | ns | P ≤ 0.01 | P ≤ 0.01 | P ≤ 0.01 |
| Stolon: length of leaf blade on fourth visible node from stolon tip (mm) | | | | | |
| Mean | 13.04 | 11.78 | 19.30 | 16.79 | 15.18 |
| Std. Deviation | 4.60 | 5.52 | 6.46 | 4.18 | 3.59 |
| LSD/sig | 2.60 | ns | P ≤ 0.01 | P ≤ 0.01 | ns |
| Stolon: width of leaf blade on fourth visible node from stolon tip (mm) | | | | | |
| Mean | 4.48 | 4.40 | 5.71 | 5.65 | 4.46 |
| Std. Deviation | 1.20 | 1.69 | 1.49 | 1.21 | 1.43 |
| LSD/sig | 0.78 | ns | P ≤ 0.01 | P ≤ 0.01 | ns |
| Flowering tiller: length of sheath on flag leaf on flowering tillers (mm) | | | | | |
| Mean | 36.74 | * | 36.90 | * | 34.11 |
| Std. Deviation | 6.04 | * | 6.92 | * | 7.07 |
| LSD/sig | 3.93 | * | ns | * | ns |
| Flowering tiller: length of blade on flag leaf on flowering tillers (mm) | | | | | |
| Mean | 17.47 | * | 23.82 | * | 19.91 |
| Std. Deviation | 6.15 | * | 6.74 | * | 6.27 |
| LSD/sig | 12.91 | * | ns | * | ns |
| Flowering tiller: width of blade on flag leaf on flowering tillers (mm) | | | | | |
| Mean | 5.25 | * | 6.29 | * | 5.49 |
| Std. Deviation | 0.94 | * | 0.90 | * | 0.78 |
| LSD/sig | 0.45 | * | P ≤ 0.01 | * | ns |
| Flowering tiller: length of sheath on fourth leaf on flowering tillers (mm) | | | | | |
| Mean | 19.12 | * | 20.98 | * | 18.94 |
| Std. Deviation | 4.01 | * | 5.66 | * | 5.54 |
| LSD/sig | 2.91 | * | ns | * | ns |
| Flowering tiller: length of blade on fourth leaf on flowering tillers (mm) | | | | | |
| Mean | 29.64 | * | 40.09 | * | 36.77 |
| Std. Deviation | 8.99 | * | 9.89 | * | 12.84 |
| LSD/sig | 4.78 | * | P ≤ 0.01 | * | P ≤ 0.01 |

TABLE 3-continued

| Characteristic | TBLL | B12 | Sir Walter | SS100 | TF01 |
|---|---|---|---|---|---|
| Flowering tiller: width of blade on fourth leaf on flowering tillers (mm) | | | | | |
| Mean | 6.25 | * | 7.36 | * | 6.74 |
| Std. Deviation | 1.21 | * | 1.29 | * | 2.11 |
| LSD/sig | 0.73 | * | P ≤ 0.01 | * | ns |
| Flowering tiller: length of fourth internode on flowering tiller (mm) | | | | | |
| Mean | 15.48 | * | 19.68 | * | 14.08 |
| Std. Deviation | 5.33 | * | 7.65 | * | 6.65 |
| LSD/sig | 3.48 | * | P ≤ 0.01 | * | ns |
| Flowering tiller: diameter of fourth internode on flowering tillers (mm) | | | | | |
| Mean | 1.69 | * | 1.69 | * | 1.79 |
| Std. Deviation | 0.28 | * | 0.28 | * | 0.25 |
| LSD/sig | 0.13 | * | ns | * | ns |
| Flowering tiller: length of peduncle on flowering tillers (mm) | | | | | |
| Mean | 41.04 | * | 42.70 | * | 26.01 |
| Std. Deviation | 12.23 | * | 13.72 | * | 8.62 |
| LSD/sig | 5.78 | * | ns | * | P ≤ 0.01 |
| Flowering tiller: diameter of peduncle on flowering tillers (mm) | | | | | |
| Mean | 1.40 | * | 1.48 | * | 1.37 |
| Std. Deviation | 0.20 | * | 0.19 | * | 0.24 |
| LSD/sig | 0.10 | * | ns | * | ns |
| Inflorescence: mean spike length (mm) | | | | | |
| Mean | 69.34 | * | 76.75 | * | 69.00 |
| Std. Deviation | 7.57 | * | 7.72 | * | 8.07 |
| LSD/sig | 4.00 | * | P ≤ 0.01 | * | ns |
| Inflorescence: mean spike width (mm) | | | | | |
| Mean | 3.99 | * | 4.30 | * | 3.89 |
| Std. Deviation | 0.52 | * | 0.49 | * | 0.49 |
| LSD/sig | 0.26 | * | P ≤ 0.01 | * | ns |
| Inflorescence: mean spike breadth (mm) | | | | | |
| Mean | 2.03 | * | 2.24 | * | 2.05 |
| Std. Deviation | 0.21 | * | 0.31 | * | 0.34 |
| LSD/sig | 0.16 | * | P ≤ 0.01 | * | ns |
| Flowering tiller: number of spikes present on inflorescence bearing tillers | | | | | |
| Mean | 2.38 | * | 2.40 | * | 1.77 |
| Std. Deviation | 0.69 | * | 0.74 | * | 0.67 |
| LSD/sig | 0.36 | * | ns | * | P ≤ 0.01 |
| Inflorescence: inflorescence density (number per $m^2$) | | | | | |
| Mean | 50.13 | * | 22.90 | * | 3.70 |
| Std. Deviation | 28.45 | * | 16.26 | * | 4.47 |
| LSD/sig | 9.74 | * | P ≤ 0.01 | * | P ≤ 0.01 |
| Sward: unmown sward height 203 days post planting (cm) | | | | | |
| Mean | 13.13 | 8.97 | 13.47 | 6.77 | 9.13 |
| Std. Deviation | 2.90 | 1.81 | 3.21 | 1.72 | 2.01 |
| LSD/sig | 1.61 | P ≤ 0.01 | ns | P ≤ 0.01 | P ≤ 0.01 |

As shown in Table 3, St. Augustine grass variety TBLL significantly differs from commercial St. Augustine grass varieties in a number of characteristics, including stolon length of fourth internode from stolon tip, length of leaf sheath on fourth visible node from stolon tip, length of blade on fourth leaf on flowering tillers, and inflorescence density.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

A deposit of the NEW FRONTIER BRANDS PTY LTD proprietary ST. AUGUSTINE GRASS NAMED TBLL disclosed above and recited in the appended claims has been made with the American Type Culture Collection (ATCC), 10801 University Boulevard, Manassas, Va. 20110 under the terms of the Budapest Treaty. The date of deposit was Oct. 7, 2015. The deposit of 2,500 seeds was taken from the same deposit maintained by NEW FRONTIER BRANDS PTY LTD since prior to the filing date of this application. All restrictions will be irrevocably removed upon granting of a patent, and the deposit is intended to meet all of the requirements of 37 C.F.R. §§1.801-1.809. The ATCC Accession Number is PTA-122562. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A seed of St. Augustine grass variety TBLL, wherein a representative sample seed of said variety is deposited under ATCC Accession Number PTA-122562.

2. A St. Augustine grass plant, or a part thereof, produced by growing the seed of claim 1.

3. A tissue culture of cells produced from the plant of claim 2, wherein said cells of the tissue culture are produced from a plant part selected from the group consisting of embryos, meristematic cells, leaf, pollen, cotyledon, hypocotyl, root, root tip, pistil, anther, flower, shoot, stem, and leaf sheath.

4. A St. Augustine grass plant regenerated from the tissue culture of claim 3, wherein the plant has all of the morphological and physiological characteristics of St. Augustine grass variety TBLL.

5. Progeny of the plant of claim 2, said progeny having all of the physiological and morphological characteristics of St. Augustine grass variety TBLL.

6. A sod, comprising the grass plant of claim 2.

7. The St. Augustine grass plant of claim 2, further comprising at least one transgene, wherein said plant comprises said transgene and otherwise comprises all of the morphological and physiological characteristics of St. Augustine grass variety TBLL.

8. A method for producing a St. Augustine grass seed, said method comprising crossing two St. Augustine grass plants and harvesting the resultant St. Augustine grass seed, wherein at least one St. Augustine grass plant is the St. Augustine grass plant of claim 2.

9. A St. Augustine grass seed produced by the method of claim 8.

10. A St. Augustine grass plant, or a part thereof, produced by growing said seed of claim 9.

11. A method for producing a St. Augustine grass seed, said method comprising crossing two St. Augustine grass plants and harvesting the resultant St. Augustine grass seed, wherein at least one St. Augustine grass plant is the St. Augustine grass plant of claim 7.

12. A method of producing an herbicide resistant St. Augustine grass plant, wherein said method comprises introducing a gene conferring herbicide resistance into the plant of claim 2.

13. A herbicide resistant St. Augustine grass plant produced by the method of claim 12, wherein the gene confers resistance to a herbicide selected from the group consisting of glyphosate, sulfonylurea, imidazolinone, dicamba, glufosinate, phenoxy proprionic acid, L-phosphinothricin, cyclohexone, cyclohexanedione, triazine, aryloxyphenoxy propionate, and benzonitrile, wherein said plant comprises said gene and otherwise comprises all of the morphological and physiological characteristics of St. Augustine grass variety TBLL.

14. A method of producing a pest or insect resistant St. Augustine grass plant, wherein said method comprises introducing a gene conferring pest or insect resistance into the St. Augustine grass plant of claim 2.

15. A pest or insect resistant St. Augustine grass plant produced by the method of claim 14, wherein said plant comprises said gene and otherwise comprises all of the morphological and physiological characteristics of St. Augustine grass variety TBLL.

16. The St. Augustine grass plant of claim 15, wherein the gene encodes a *Bacillus thuringiensis* (Bt) endotoxin.

17. A method of producing a disease resistant St. Augustine grass plant, wherein said method comprises introducing a gene which confers disease resistance into the St. Augustine grass plant of claim 2.

18. A disease resistant St. Augustine grass plant produced by the method of claim 17, wherein said plant comprises said gene and otherwise comprises all of the morphological and physiological characteristics of St. Augustine grass variety TBLL.

19. A method of introducing a desired trait into St. Augustine grass variety TBLL, wherein the method comprises:
   a. crossing a TBLL plant, wherein a representative sample of seed is deposited under ATCC Accession Number PTA-122562, with a plant selected from the group consisting of another St. Augustine grass variety, another species of *Stenotaphrum*, and another plant genus that comprises a desired trait to produce progeny plants;
   b. selecting one or more progeny plants that have the desired trait to produce selected progeny plants;
   c. backcrossing the selected progeny plants with St. Augustine grass variety TBLL to produce backcross progeny plants;
   d. selecting for backcross progeny plants that have the desired trait and otherwise all of the morphological and physiological characteristics of St. Augustine grass variety TBLL; and
   e. repeating steps c and d two or more times in succession to produce selected third or higher backcross progeny plants that comprise the desired trait.

20. A St. Augustine grass plant produced by the method of claim 19, wherein the plant has the desired trait and otherwise all of the physiological and morphological characteristics of St. Augustine grass variety TBLL.

* * * * *